United States Patent [19] [11] Patent Number: 4,820,832
Cook et al. [45] Date of Patent: Apr. 11, 1989

[54] PROCESS FOR PREPARING 3-UNSUBSTITUTED CEPHALOSPORINS AND 1-CARBA(DETHIA)CEPHALOSPORINS

[75] Inventors: Gwendolyn K. Cook; John H. McDonald, III, both of Indianapolis, Ind.

[73] Assignee: Eli Lilly and Company, Indianapolis, Ind.

[21] Appl. No.: 172,099

[22] Filed: Mar. 23, 1988

[51] Int. Cl.$^4$ .............................. C07D 501/04
[52] U.S. Cl. .................. 540/205; 540/215; 540/219; 540/222
[58] Field of Search .............. 540/215, 219, 222, 205; 514/210, 192

[56] References Cited

U.S. PATENT DOCUMENTS

| | | | |
|---|---|---|---|
| 4,343,943 | 10/1982 | Hirata et al. | 540/205 |
| 4,436,903 | 3/1984 | Sedelmerer et al. | 540/215 |
| 4,647,658 | 3/1987 | Hamashima et al. | 540/215 |
| 4,665,171 | 5/1987 | Evans et al. | 540/364 |
| 4,673,737 | 6/1987 | Evans et al. | 540/205 |

FOREIGN PATENT DOCUMENTS 84111916.7 10/1984 European Pat. Off. .

OTHER PUBLICATIONS

Chemical Abstracts, vol. 87: 135362m (1977).

Primary Examiner—Nicholas S. Rizzo
Attorney, Agent, or Firm—William B. Scanlon; Leroy Whitaker

[57] ABSTRACT

A process for preparing 7$\beta$-acylamino (or 7$\beta$-protected amino)-3-H-1-carba(1-dethia)-3-cephem-4-carboxylic acid esters and the corresponding cephalosporins is provided. 7$\beta$-Acylamino (or 7$\beta$-protected amino)-3-halo (or 3-sulfonyl ester)-1-carba(dethia)-3-cephem carboxylic acid esters and the corresponding cephalosporins are reduced with Pd(O) and a tetra-$C_2$-$C_6$ alkyl stannane and, when a 3-sulfonyloxy ester is reduced, the process is carried out in the presence of an alkali metal halide. 3-Sulfonyloxy-3-cephem esters such as 3-mesylate, 3-tosylate and 3-triflate are employed.

13 Claims, No Drawings

PROCESS FOR PREPARING 3-UNSUBSTITUTED CEPHALOSPORINS AND 1-CARBA(DETHIA)CEPHALOSPORINS

BACKGROUND OF THE INVENTION

This invention relates to a process for preparing β-lactam antibiotics. In particular, it relates to a process for preparing 7β-acylamino (or 7β-protected amino)-3-H cephalosporins and the corresponding 1-carba(dethia)cephalosporins.

Hamashima, in European Patent Application No. 84111916.7, teaches that 3-hydrogen cephalosporins are useful as antibacterial agents in treating infectious diseases in man and animals. Further, among the newer β-lactam antibiotics currently under evaluation are the 1-carba(1-dethia)-3-cephem-4-carboxylic acids. Preparation of these compounds in particular provide considerable synthetic challenges. Among the approaches for synthesis of 1-carba(1-dethia)cephalosporins is the asymmetric process described by Evans, et al., U.S. Pat. No. 4,665,171. Because of the importance of the continued development of β-lactam antibiotics for the treatment of infectious disease, processes for the preparation of such antibiotics are of considerable importance.

SUMMARY

7β-Acylamino (and 7β-protected amino)-3-hydrogen-1-carba(1-dethia)cephalosporins and the corresponding cephalosporins are produced in a process comprising the Pd(O) catalyzed reduction of a 7β-acylamino (and 7β-protected amino)-1-carba(1-dethia) or corresponding cephalosporin substituted in the 3-position by a halogen or a sulfonyloxy ester group, including a 3-mesylate, tosylate or triflate cephalosporin with a tetra-alkyl stannane in the presence of an alkali metal halide. The products of the reaction may themselves be useful as β-lactam antibiotics or may be useful as intermediates in the synthesis of other β-lactam antibiotics.

DETAILED DESCRIPTION

According to this invention there is provided a process for preparing a compound represented by Formula 1

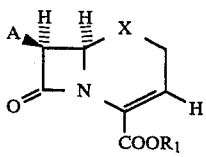
(1)

wherein A is a protected amino group or an acylamino group R(CO)NH—; X is sulfur or —$CH_2$—; and $R_1$ is a carboxy-protecting group; which comprises reacting a compound of Formula (2)

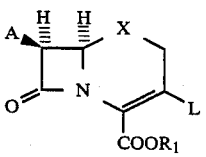
(2)

wherein A, X and $R_1$ are as defined above; L is trifluoromethanesulfonyloxy, methanesulfonyloxy, p-toluenesulfonyloxy, chloro, bromo or iodo; in an inert solvent in the presence of palladium (O) with a tetra-$C_2$ to $C_6$ alkyl stannane and in the presence of an alkali-metal halide when L is trifluoromethanesulfonyloxy, methanesulfonyloxy or p-toluenesulfonyloxy.

The process is carried out at a temperature between about −5° C. and about 80° C., preferably at about 60° C. to about 70° C.

Inert solvents which can be used are polar organic solvents of sufficient polarity to maintain substantially all of the reagents and reactants in solution. Solvents that can be used are dimethylformamide, dimethylacetamide, acetonitrile and like aprotic organic solvents.

The palladium catalyst employed in the process is Pd(O) which is soluble or partially soluble in the inert solvent and which can be generated in situ or provided in the form of a Pd(O) compound such as tetrakis-(triphenylphosphine)palladium (O). Reagents that can be used as sources of Pd(O) are, for example, the combination of palladium diacetate-triphenylphosphine and a tertiary amine such as triethylamine or N-methylmorpholine; palladium dichloride diacetonitrilate; and tetrakis-(triphenylphosphine)palladium (O). Other palladium compounds which can be reduced to Pd(O) are known and may be used in the process if otherwise compatible with the reactants. It is sometimes found to be efficacious to initiate in situ generation of Pd(O) with a small (approximately catalytic) amount of tetravinyl tin or hexamethyldistannane.

The process is carried out under substantially anhydrous conditions with the reaction vessel, solvent, starting material and reagents being substantially dry.

The process is generally performed by adding the palladium (O) compound or the Pd(O) generating reagents to a solution of a compound of Formula (2) in the inert solvent, about 0.1 to 0.2 equivalents followed by the addition of the tetra-alkylstannane. When the starting material 2 is a 3-sulfonyloxy derivative, i.e. when L is trifluoromethanesulfonyloxy, methanesulfonyloxy or p-toluenesulfonyloxy, approximately 2 equivalents of an alkali metal halide are also added to the mixture. The reaction mixture is then heated with stirring until complete. The reaction mixture is preferably covered by dry nitrogen during the process to exclude atmospheric moisture and oxygen. As noted above, a halide source is not necessary if, in Formula (2), L is chloro, bromo or iodo.

Alkali metal halides which can be used are lithium bromide, lithium chloride, sodium bromide, sodium chloride, potassium bromide and the like. Of course, one skilled in the art will appreciate that other halide sources would be efficacious, e.g., a tetraalkyl ammonium halide such as tetramethyl ammonium chloride.

Tetra-alkyl stannane compounds which can be used in the process include, for example, tetra-ethyl stannane, tetra-n-propyl stannane, tetra-n-butyl stannane, tetra-n-pentyl stannane, tetra-n-hexyl stannane, tetra-isobutyl stannane, tetra-isopentyl stannane, tetra-isohexyl stannane and like tetra-$C_2$-$C_6$ alkyl stannane compounds. The only limitation on the alkyl portion of the reagent is that the carbon attached to the tin must be a primary carbon.

Preferred inert solvents are dimethylformamide and dimethylacetamide. Lithium halides are preferred, especially lithium chloride. A preferred $C_2$ to $C_6$ alkyl stannane is tetra-n-butyl stannane.

It is often desirable to utilize a free radical scavenger in the reaction mixture, for example, 2,6-di-t-butyl-4- methyl phenol. Other scavengers which can be used include, for example, butylated hydroxyanisole.

In an example of the process, benzhydryl 7β-phenoxyacetylamino-3-trifluoromethylsulfonyloxy-1-carba(1-dethia)-3-cephem-4-carboxylate is dissolved in dimethylformamide and 0.1 equivalent of palladium dichloride diacetonitrilate is added along with 2.0 equivalents of LiCl. The reaction mixture is flushed repeatedly with $N_2$ and then is treated with 1.3 equivalents of tetra-n-butyl tin and 0.1 equivalent of 2,6-di-t-butyl-4-methyl phenol and heated to approximately 70° C. At this point, a catalytic amount of tetravinyl tin is added in order to initiate reduction of the Pd(II) to Pd(O). The reaction is generally complete within one hour.

The progress of the reaction may be followed by running thin layer chromatography on small aliquots of the reaction mixture from time to time. The 3-H-3-cephem compounds of formula (2) may be recovered from the reaction mixture by conventional isolation procedures. For example, the reaction mixture may be diluted with a water immiscible organic solvent such as ethyl acetate, the solution washed with dilute acid and bicarbonate and, after drying, evaporated to provide the reaction product in crude form. The product may be purified by chromatography, e.g., over silica.

Examples of 3-H compounds of Formula (1) which can be prepared using the present invention include p-nitrobenzyl 7β-phenoxyacetylamino-3-H-1-carba(1-dethia)3-cephem-4-carboxylate, p-methoxybenzyl 7β-phenyl- acetylamino-3-H-1-carba(1-dethia)-3-cephem-4-carboxylate, diphenylmethyl 7β-t-butyloxycarbonylamino-3-H-1-carba-(1-dethia)-3-cephem-4-carboxylate; t-butyl 7β-benzyl- oxycarbonylamino-3-H-1-carba(1-dethia)-3-cephem-4-carboxylate, benzyl 7β-formamido-3-H-1-carba(1-dethia)-3-cephem-4-carboxylate; benzhydryl 7β-phenoxyacetyl amino-3-H-1-carba(1-dethia)-3-cephem-4-carboxylate, p-nitrobenzyl 7β-phenoxyacetylamino-3-H-3-cephem-4-carboxylate; p-nitrobenzyl 7β-t-butyloxycarbonylamino-3-H-3-cephem-4-carboxylate; and t-butyl 7β-t-butyloxy carbonylamino-3-H-3-cephem-4-carboxylate.

The 1-carba-3-triflates of Formula (2) used as one of the possible starting materials in the process are prepared by the method described by Evans et al. U.S. Pat. No. 4,673,737. The tosylate and mesylate esters of Formula (2) are known compounds readily obtained with the 3-OH compounds.

Although the mechanism by which the process of this invention proceeds is uncertain, it may be described as a palladium catalyzed reduction. The nature of the process suggests palladium insertion followed by hydride transfer and reductive elimination.

In Formula (1), when A is an acylamino group R(CO)NH—, R is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, or trifluoromethylthio; a phenyl or substituted phenyl group represented by the formula

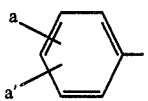

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, mono- or di($C_1$-$C_4$ alkyl)amino, $C_1$-$C_4$ alkanoylamino, $C_1$-$C_4$ alkylsulfonylamino, carboxy, carbamoyl, hydroxymethyl, aminomethyl, or carboxymethyl;

a group represented by the formula

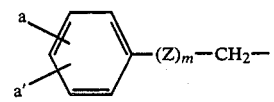

wherein a and a' have the same meanings as defined above, Z is O or S, and m is 0 or 1;

a heteroarylmethyl group represented by the formula

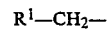

wherein $R^1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino;

a substituted methyl group represented by the formula

wherein $R^2$ is cyclohex-1,4-dienyl, or a phenyl group or substituted phenyl group

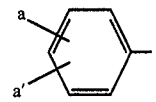

wherein a and a' have the above defined meanings, or $R^2$ is $R^1$ as defined above, and Q is hydroxy, $C_1$-$C_4$ alkanoyloxy, carboxy, sulfo, or amino;

or R is a keto group or an oximino-substituted group represented by the formulae

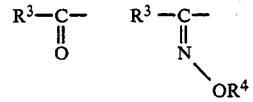

wherein $R^3$ is $R^1$ or $R^2$ as defined above and $R^4$ is hydrogen, $C_1$-$C_4$ alkyl, or a carboxy-substituted alkyl or cycloalkyl group represented by the formula

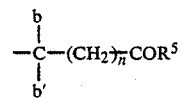

wherein b and b' independently are hydrogen, or $C_1$-$C_3$ alkyl, and b and b' when taken together with the carbon to which they are bonded form a 3- to 6-membered carbocyclic ring, and $R^5$ is hydroxy, $C_1$-$C_4$ alkoxy, amino, $C_1$-$C_4$ alkylamino, or di($C_1$-$C_4$ alkyl)amino.

In the above definition of the compounds represented by Formula (1), $C_1$-$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$-$C_6$ alkyl substituted by cyano refers to cyanomethyl, cyanoethyl, 4-cyanobutyl, and the like; $C_1$-$C_6$ alkyl substituted by carboxy refers to such groups as carboxymethyl, 2-carboxyethyl, 2-carboxypropyl, 4-carboxybutyl, 5-carboxypentyl, and the like; $C_1$-$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$-$C_6$ alkyl substituted by amino refers to such groups as 2-aminoethyl, aminomethyl, 3-aminopropyl and 4-aminobutyl; $C_1$-$C_6$ alkyl substituted by $C_1$-$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like group; $C_1$-$C_6$ alkyl substituted by $C_1$-$C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$-$C_6$ alkyl substituted by trifluoromethyl is exemplified by 2,2,2-trifluoroethyl, 3,3,3-trifluoropropyl, 4,4,4-trifluorobutyl, and the like; and $C_1$-$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$-$C_6$ alkyl substituted groups.

When in Formula (1) R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such a 3-methylsulfonylamino, 4-methylsulfonylamino, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO- groups of Formula (1) wherein R is a group represented by the formula

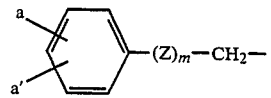

with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^1$-$CH_2CO$ groups of Formula (1) wherein $R^1$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups optionally substituted by amino, $C_1$-$C_4$ alkylsulfonylamino, hydroxy, halo, $C_1$-$C_4$ alkyl or $C_1$-$C_4$-alkoxy groups.

Examples of RCO- groups of Formula (1) compounds wherein R is a substituted methyl group represented by the formula $R^2$-CH(Q)- and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl; 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl.

Examples of RCO acyl groups of the compounds represented by Formula (1) when R is a keto group or an oximino-substituted group represented by the formulae

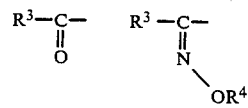

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)-iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoyl-prop-2-yl)oxyiminoacetyl, and 2-(5-amino-1,3,4-thiadia- zol-2-yl)-2-methoxyiminoacetyl.

The starting material (2) desirably has any free amino or carboxy functions which may be present in the R(CO) group in protected form, e.g., protected with an $R_1$ protecting group or a protected amino group as defined below.

The carboxy-protecting group $R_1$ is a conventional carboxy-blocking group used in the β-lactam antibiotic art and serves the function of blocking the acidic carboxy group while reactions are carried out at other sites in the molecule. Such groups are used for the temporary protection or blocking of the carboxy group. Examples of such groups are t-butyl, haloalkyl groups, e.g. 2,2,2-trichloroethyl or 2-iodoethyl; benzyl, and substituted benzyl, e.g. 4-nitrobenzyl, and 4-methoxybenzyl, diphenylmethyl, trialkylsilyl or mixed alkylarylsilyl groups, e.g. trimethylsilyl, triethylsilyl, dimethylphenylsilyl, β-trimethylsilylethyl, and β-methylsulfonylethyl.

Protected amino groups represented by A in Formulas 1 and 2 are the conventional protecting or blocking groups used in the β-lactam antibiotic art for the temporary protection of the amino group function while reactions at other sites in the molecule are carried out. Examples of suitable protecting groups are formyl, trichloroacetyl, tribromoacetyl, trityl, an alkyl, cycloalkyl, or aryloxycarbonyl group such as ethoxycarbonyl, t-butyloxycarbonyl, trichloroethoxycarbonyl, cyclopentyloxycarbonyl, benzyloxycarbonyl, p-nitrobenzyloxycarbonyl, and diphenylmethoxycarbonyl; allyloxycarbonyl, a bicyclooxycarbonyl group such as adamantyloxycarbonyl or bicycloheptyloxycarbonyl; an enamine group, for example, those formed from methylacetoacetate or ethylacetoacetate; or other conventional amino-protecting groups. Preferred amino-protecting groups A are represented by the formula

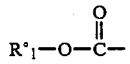

wherein $R°_1$ is $C_1-C_4$-alkyl, $C_3-C_7$ cycloalkyl, benzyl, nitrobenzyl, halobenzyl or methoxybenzyl. Preferred amino-protecting groups are benzyloxycarbonyl, p-nitrobenzyloxycarbonyl, and t-butyloxycarbonyl.

In a preferred process of this invention, A is an acylamino group R(CO)NH-. Especially preferred acylamino groups are phenoxyacetyl and phenylacetyl. Further preferred are 3-triflates and 3-halogens (2), and 3-hydrogen compounds (1) wherein A is a protected amino group, especially t-butyloxycarbonylamino or benzyloxycarbonylamino.

The following Examples are provided to further illustrate the invention and are not to be construed as limiting thereof.

EXAMPLE 1

Benzhydryl 7β-phenoxyacetylamino-3-hydrogen-1-carba(dethia)-3-cephem-4-carboxylate A 200 mg portion (0.317 mmol) of benzhydryl 7β-phenoxyacetylamino-3-trifluoromethylsulfonyloxy-1-carba(dethia)-3-cephem-4-carboxylate was dissolved in 0.63 ml of dimethylformamide. The solution of starting material was then treated with 27 mg (0.634 mmol; 2.0 equivalents) of lithium chloride and 8 mg (0.1 equivalent) of palladium dichloride diacetonitrilate. The reaction vessel was then flushed with $N_2$ repeatedly. Finally, the reaction mixture was treated with 7 mg (0.0317 mmol); 0.1 equivalent) of 2,6-di-t-butyl-4-methylphenol and 143 mg (135 μl; 0.412 mmol; 1.3 equivalents) of tetra-n-butyl tin and the solution was heated to approximately 70° C., at which point a 5 μl sample of tetravinyl tin was added.

After about 1.5 h the reaction mixture was cooled to room temperature and diluted with ethyl acetate, and filtered through celite. The resulting solution was further diluted with ether and then washed with water (3 times). The organic phase was dried over anhydrous $MgSO_4$, filtered and concentrated in vacuo. The crude product was dissolved in $CH_3CN$ and washed 5 times with hexane. The $CH_3CN$ solution was concentrated in vacuo and the resulting crude product chromatographed over silica gel (50% ethyl acetate/hexane) to provide 139 mg (91% yield) of the title compound.

NMR (300 mhz): (CDCl$_3$) 1.30–1.50 (1H, m), 1.83–1.97 (1H, m), 2.17–2.43 (2H, m), 3.77–3.87 (1H, m), 4.57 (2H, s), 5.47 (1H, d of doublets), 6.50–6.55 (1H, m), 6.83–7.05 (3H, m), 7.20–7.53 (14H, m).

EXAMPLE 2 p-Nitrobenzyl 7β-phenoxyacetylamino-3-H-3-cephem-4-carboxylate

A 100 mg sample (0.18 mmol; 1.0 equivalent) of p-nitrobenzyl 7β-phenoxyacetylamino-3-bromo-3-cephem-4-carboxylate was dissolved in 0.4 ml of anhydrous dimethylformamide and treated with 69 mg (65 μl; 0.198 mmol; 1.1 equivalents) of tetra-n-butyl stannane, followed by 5 mg (0.018 m mol; 0.1 equivalent) of palladium dichloride diacetonitrilate and a catalytic amount of tetravinyl stannane. After 0.5 h of stirring at room temperature, the reaction mixture was heated to about 60° C. overnight.

The crude reaction mixture was diluted with a 1:1 ethyl acetate/diethyl ether mixture and washed (3×) with water. The organic solution was then dried over anhydrous $MgSO_4$, filtered and concentrated in vacuo. The resulting residue was triturated (3×) with hexane and chromatographed over silica gel (using 55% hexane/45% ethyl acetate as eluent) to provide 33 mg (44% yield) of the title compound.

NMR (300 mhz): (CDCl$_3$) 3.33–3.63 (2H, m), 4.53 (2H, s), 4.93 (1H, d), 5.23 (1H, d), 5.40 (1H, d), 5.95–6.0 (1H, m), 6.53–6.63 (1H, m), 6.83 (2H, d), 6.93 (1H, t), 7.17–7.37 (3H, m), 7.50 (2H, d), 8.17 (2H, d).

EXAMPLE 3 t-Butyl 7β-phenoxyacetylamino-1-carba(1-dethia)-3-H-3-cephem-4-carboxylate

In a manner analogous to that of Example 1, t-butyl 7β-phenoxyacetylamino-1-carba(1-dethia)-3-iodo-3-cephem-4-carboxylate is converted to the title compound.

EXAMPLE 4 t-Butyl 7β-t-butyloxycarbonylamino-1-carba(1-dethia)-3-H-3-cephem-4-carboxylate In a procedure analogous to that of Example 1, t-butyl 7β-t-butyloxycarbonylamino-1-carba(1-dethia)-3-bromo-3-cephem-4-carboxylate is converted to the title compound.

We claim:

1. A process for preparing a compound of the formula

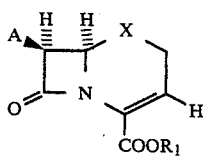

wherein A is a protected amino group or an acylamino group R(CO)NH; X is sulfur or —CH$_2$—; and R$_1$ is a carboxy-protecting group; which comprises reacting a 3-cephem ester of the formula

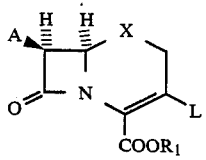

wherein A, X and R$_1$ have the same meanings as defined above, L is trifluoromethanesulfonyloxy, methanesulfonyloxy, p-toluenesulfonyloxy, chloro, bromo or iodo in an inert solvent in the presence of palladium (O) with tetra-(C$_2$-C$_6$ alkyl) stannane and in the presence of an alkli metal halide when L is trifluoromethanesulfonyloxy, methanesulfonyloxy or p-toluenesulfonyloxy.

2. The process of claim 1 where, in the acylamino group A, R is hydrogen; C$_1$-C$_6$ alkyl, C$_1$-C$_6$ alkyl substituted by cyano, carboxy, halogen, amino, C$_1$-C$_4$ alkoxy, C$_1$-C$_4$ alkylthio, or trifluoromethylthio; a phenyl or substituted phenyl group represented by the formula

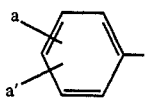

wherein a and a' independently are hydrogen, halogen, hydroxy, C$_1$-C$_4$ alkoxy, C$_1$-C$_4$ alkanoyloxy, C$_1$-C$_4$ alkyl, C$_1$-C$_4$ alkylthio, amino, mono- or di(C$_1$-C$_4$ alkyl)amino, C$_1$-C$_4$ alkanoylamino, C$_1$-C$_4$ alkylsulfonylamino, carboxy, carbamoyl, hydroxymethyl, aminomethyl, or carboxymethyl;

a group represented by the formula

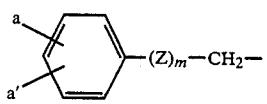

wherein a and a' have the same meanings as defined above, Z is O or S, and m is 0 or 1;

a heteroarylmethyl group represented by the formula

wherein R$^1$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, C$_1$-C$_4$ alkyl, C$_1$-C$_4$ alkoxy, C$_1$-C$_4$ alkylsulfonylamino;

a substituted methyl group represented by the formula

wherein R$^2$ is cyclohex-1,4-dienyl, or a phenyl group or substituted phenyl group represented by the formula

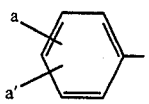

wherein a and a' have the above defined meanings, or R$^2$ is R$^1$ as defined above, and Q is hydroxy, C$_1$-C$_4$ alkanoyloxy, carboxy, sulfo, or amino;

or R is a keto group or an oximino-substituted group represented by the formulae

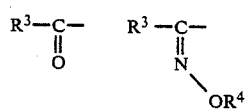

wherein R$^3$ is R$^1$ or R$^2$ as defined above and R$^4$ is hydrogen, C$_1$-C$_4$ alkyl, or a carboxysubstituted alkyl or cycloalkyl group represented by the formula

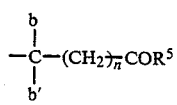

wherein b and b' independently are hydrogen, or C$_1$-C$_3$ alkyl, and b and b' when taken together with the carbon to which they are bonded form a 3- to 6-membered carbocyclic ring, and R$_5$ is hydroxy, C$_1$-C$_4$ alkoxy, amino, C$_1$-C$_4$ alkylamino, or di(C$_1$-C$_4$ alkyl)amino.

3. The process of claim 1 wherein A is a protected amino group.

4. The process of claim 2 wherein R is benzyl or phenoxymethyl.

5. The process of claim 1 wherein R$_1$ is benzyl, p-nitrobenzyl, p-methylbenzyl or diphenylmethyl.

6. The process of claim 3 wherein A is t-butyloxycarbonyl or benzyloxycarbonyl.

7. The process of claim 1 wherein the solvent is dimethylformamide or dimethylacetamide.

8. The process of claim 1 wherein L is chloro, bromo or iodo.

9. The process of claim 1 wherein L is trifluoromethanesulfonyloxy, methanesulfonyloxy or p-toluenesulfonyloxy.

10. The process of claim 9 wherein the alkali metal halide is lithium chloride.

11. The process of claim 1 wherein the Pd(O) is generated in situ from palladium dichloride diacetonitrilate and tetra-n-butyl stannane.

12. The process of claim 6 wherein A is t-butoxycarbonyl and $R_1$ is benzhydryl.

13. The process of claim 10 wherein X is —$CH_2$—.

* * * * *